United States Patent
Anciaux et al.

(10) Patent No.: US 9,746,483 B2
(45) Date of Patent: Aug. 29, 2017

(54) PROCESS FOR THE PRODUCTION OF A HYBRIDOMA AND ANTIBODY OBTAINED THEREFROM, ABLE TO RECOGNIZE MORE THAN ONE VITAMIN D METABOLITE

(71) Applicant: Diasource Immunoassays S.A., Nivelles (BE)

(72) Inventors: Michel Anciaux, Nalinnes (BE); Fabienne Mathieu, Nivelles (BE); Frederic Lin, Bousval (BE); Martin Poncelet, Louvain-la-Neuve (BE)

(73) Assignee: DIASOURCE IMMUNOASSAYS S.A., Nivelles (BE)

( * ) Notice: Subject to any disclaimer, the term of this patent is extended or adjusted under 35 U.S.C. 154(b) by 176 days.

(21) Appl. No.: 14/708,594

(22) Filed: May 11, 2015

(65) Prior Publication Data
US 2015/0346224 A1 Dec. 3, 2015
US 2017/0067916 A9 Mar. 9, 2017

Related U.S. Application Data

(63) Continuation of application No. 12/911,924, filed on Oct. 26, 2010, now abandoned.

(60) Provisional application No. 61/255,164, filed on Oct. 27, 2009.

(51) Int. Cl.
| | |
|---|---|
| G01N 33/82 | (2006.01) |
| C07K 16/44 | (2006.01) |
| G01N 33/577 | (2006.01) |
| C07K 16/26 | (2006.01) |

(52) U.S. Cl.
CPC .............. *G01N 33/82* (2013.01); *C07K 16/26* (2013.01); *C07K 16/44* (2013.01); *G01N 33/577* (2013.01); *C07K 2317/24* (2013.01); *C07K 2317/33* (2013.01); *Y10T 436/203332* (2015.01)

(58) Field of Classification Search
CPC .... C07K 16/26; C07K 16/44; C07K 2317/24; C07K 2317/33; G01N 33/577; G01N 33/82; Y10T 436/203332
See application file for complete search history.

(56) References Cited

U.S. PATENT DOCUMENTS

| | | | |
|---|---|---|---|
| 4,585,741 A | 4/1986 | Clevinger et al. |
| 6,787,660 B1 | 9/2004 | Armbruster et al. |
| 7,776,544 B2 | 8/2010 | Gupta |
| 2007/0238653 A1 | 10/2007 | Owens et al. |
| 2008/0317764 A1 | 12/2008 | Huber et al. |

FOREIGN PATENT DOCUMENTS

| | | |
|---|---|---|
| DE | 10144905 A1 | 4/2003 |
| EP | 0 092 004 B1 | 10/1985 |
| EP | 1 097 132 B1 | 12/2003 |
| WO | 94/24304 A1 | 10/1994 |
| WO | 03/023391 A2 | 3/2003 |
| WO | 2007/039193 A1 | 4/2007 |
| WO | 2007/039194 A1 | 4/2007 |
| WO | 2008/092917 A1 | 8/2008 |

OTHER PUBLICATIONS

Aarden (Mar. 12, 2016) "Expert Report of Professor Aarden," Report Prepared for Opposition Proceedings in European Patent Application No. 10189130.7, 17 pgs.
Aarden. Curriculum vitae of Professor Lucien A. Aarden Prepared for Opposition Proceedings in European Patent Application No. 10189130.7 beginning on Aug. 11, 2015, 2 pgs.
ALPCO Diagnostics (Feb. 27, 2009) "Announcing the launch of the new 25-OH vitamin D ELISA: Exceptional Correlation to LC/MS in a user-friendly, automatable ELISA format," Press release. Accessible on the Internet at URL: http://www.pr.com/press-release/135952, 1 pg.
ALPCO Diagnostics (Mar. 17, 2009) "ALPCO Immunoassays: 25-OH Vitamin D ELISA," ALPCO Diagnostics, 12 pgs.
Bandeira et al. (2008) "Automated de novo protein sequencing of monoclonal antibodies," Nat. Biotechnol. 26 (12):1336-1338.
Bedzyk (Aug. 26, 2014) Declaration of Dr. William Bedzyk Prepared for Opposition Proceedings in European Patent Application No. 10189130.7, 22 pgs.
Bedzyk (May 12, 2016) Declaration of Dr. William Bedzyk Prepared for Opposition Proceedings in European Patent Application No. 10189130.7, 21 pgs.
Berg (1984) "Identification, Production, and Characterization of Murine Monoclonal Antibody (LO-22) Recognizing 12 Native Species of Human Alpha Interferon," J. Interferon Res. 4:481-491.
Berzofsky et al. (1981) "The concepts of crossreactivity and specificity in immunology," Mol. Immunol. 18 (8):751-763.
Berzofsky et al. (2003) "Antigen-Antibody Interactions and Monoclonal Antibodies," Ch. 4 In; Fundamental Immunology. 5th Ed. Ed.: Paul. pp. 69, 86-89.
Cavalier et al. (2008) "Serum vitamin D measurement may not reflect what you give to your patients" J. Bone Miner. Res. 23(11):1864-1865.
David et al. (1985) "Characterization of monoclonal antibodies against prostaglandin E2: fine specificity and neutralization of biological effects," Mol. Immunol. 22(3):339-346.
Diamond et al. (1981) "Monoclonal Antibodies—A New Technology for Producing Serologic Reagents," New Eng. J. Med. 304(22):1344-1349.
Glendenning et al. (2006) "Current assays overestimate 25-hydroxyvitamin D3 and underestimate 25-hydroxyvitamin D2 compared with HPLC: Need for Assay-Specific Decision Limits and Metabolite-Specific Assays," Ann. Clin. Biochem. 43:23-30.
Hollis (Mar. 23, 2011) Declaration Professor Bruce Hollis Prepared for Opposition Proceedings in European Patent Application No. 06805884.1, 52 pgs.

(Continued)

*Primary Examiner* — Galina Yakovleva
(74) *Attorney, Agent, or Firm* — Lathrop Gage LLP; James H. Velema, Esq.

(57) ABSTRACT

The invention concerns a process for the production of a hybridoma, and of a monoclonal antibody or fragments thereof able to recognize 25-hydroxyvitamin $D_2$ and 25-hydroxyvitamin $D_3$.

2 Claims, No Drawings

(56) References Cited

OTHER PUBLICATIONS

Hollis et al. (1985) "Improved radioimmunoassay for vitamin D and its use in assessing vitamin D status," Clin. Chem. 31(11):1815-1819.
Hollis et al (2000) "Comparison of Commercially Available 125I-based RIA Methods for the Determination of Circulating 25-Hydroxyvitamin D," Clin. Chem. 46(10)1657-1661.
Hollis et al. (2007) "The assessment of circulating 25(OH)D and 1,25(OH)2D: where we are and where we are going," J. Steroid Biochem. Mol. Biol. 103:473-476.
Immundiagnostik AG "Data Sheet: 25(OH) Vitamin D3, Anitbody, Monoclonal," Immundiagnostik AG. Provided in Opposition Proceedings in European Patent Application No. 10189130.7 beginning on Aug. 11, 2015, 1 pg.
Immundiagnostik AG (Feb. 12, 2009) "25(OH)-Vitamin D direct ELISA Kit Manual," Immundiagnostik AG. pp. 1-28, 16 pgs.
Immundiagnostik AG (Jun. 13, 2007) "Immunochemicals 2007," Immundiagnostik AG Sales Catalogue, 26 pgs.
Immundiagnostik AG (Oct. 16, 2009) "Manual: 25(OH)-Vitamin D direct ELISA Kit," Immundiagnostik AG. pp. 18-31, 16 pgs.
Immundiagnostik AG (Oct. 16, 2009) "Manual: 25(OH)-Vitamin D direct ELISA Kit," pp. 18-32. Also provided herewith is a Newsletter communication from Sep. 28, 2005 containing a product catalog, 22 pgs.
Immundiagnostik AG Various Invoices, Packaging Lists, Shipment and Transport Confirmations Provided in Opposition Proceedings in European Patent Application No. 10189130.7 beginning on Aug. 11, 2015, 12 pgs.
Kontermann (May 13, 2016) Declaration pf Professor Roland Kontermann Prepared for Opposition Proceedings in European Patent Application No. 10189130.7, 7 pgs.
Kontermann. Curriculum vitae and Publications Listing of Professor Roland Kontermann Prepared for Opposition Proceedings in European Patent Application No. 10189130.7 beginning on Aug. 11, 2015, 10 pgs.
Lane et al. (1982) "Molecular recognition and the future of monoclonal antibodies," Nature. 296:200-202.
Laurence et al. (1987) "Epitope Design for the Induction of Antibodies Which Recognize a Family of Molecules: Example of Monoclonal Antibodies to 2'-5' Oligoadenylates," Mol. Immunol. 24(10):1033-1038.
Liddell (2005) "Antibodies," Ch. 8 In; The Immunoassay Handbook. 3rd Ed. Eds.: Wild et al. Elsevier. pp. 149-150.
Linscott (Apr. 12, 2016) Email Correspondence of Dr. Russell Linscoll Provided in Opposition Proceedings in European Patent Application No. 10189130.7, 2 pgs.
Linscott'S Directory "Linscott's Directory of Immunological & Biological Reagents," Accessible on the Internet at URL: http://www.linscottsdirectory.com. [Last Accessed May 9, 2016], 4 pgs.
Macardle et al. (2006) "Preparation of Monoclonal Antibodies," Ch. 57 In; Cell Biology. Elsevier Sciences. pp. 475-482.
Mawer et al. (1985) "Selection of high-affinity and high-specificity monoclonal antibodies for 1 alpha,25-dihydroxyvitamin D," Steroids. 46(2-3):741-754.
Mawer et al. (1990) "A sensitive radioimmunoassay using a monoclonal antibody that is equipotent for ergocalcitriol and calcitriol (1,25-dihydroxyvitamin D2 and D3)," Clin. Chim. Acta. 190:199-210.

Mudgett-Hunter et al. (1985) "Binding and structural diversity among high-affinity monoclonal anti-digoxin antibodies," Mol. Immunol. 22(4):477-488.
Pincus et al. (1984) "Phenotypic and Genotypic Characterization of Monoclonal Anti-Digoxin Antibodies," Life Sciences. 35:433-440.
Price List of Immundiagnostik Immunochemicals dated Mar. 7, 2007, Prepared for Opposition Proceedings in European Patent Application No. 10189130.7 beginning on Aug. 11, 2015, 6 pgs.
Sahakian (May 11, 2016) Declaration Niver Sahakian Prepared for Opposition Proceedings in European Patent Application No. 10189130.7, 22 pgs.
Schumann (Apr. 18, 2011) Declaration of Claudia Schumann Prepared for Opposition Proceedings in European Patent Application No. 06805884.1.—with English translation, 3 pgs.
Schumann (Apr. 18, 2011) Declaration of Claudia Schumann Prepared for Opposition Proceedings in European Patent Application No. 10189130.7.—with English translation, 2 pgs.
Screen Capture of material found on the Internet at URL: http://www.pr.com. and http://aplco2.rssing.com/browser.php?indx=10574640&item=1, 1 pg.
Sevier et al. (1981) "Monoclonal antibodies in clinical immunology," Clin. Chem. 27(11):1797-1806.
Turpeinen et al. (2003) "Determination of 25-hydroxyvitamin D in serum by HPLC and immunoassay," Clin. Chem. 49(9):1521-1524.
U.S. Customs and Border Protection (2006) "Importing into the United States—A Guide for Commercial Importer," CBP Document No. 0000-0504. pp. 1, 12.
Wang et al. (2007) "Development of a Monoclonal Antibody-Based Broad-Specificity ELISA for Fluoroquinolone Antibiotics in Foods and Molecular Modeling Studies of Cross-Reactive Compounds," Anal. Chem. 79:4471-4483.
White et al. (1985) "Monoclonal Antibodies to Testosterone: The Effect of Immunogen Structure on Specificity," J. Steroid Biochem. 22(2):169-175.
Zola (1987) In; Monoclonal Antibodies: A Manual of Techniques. CRC Press. p. 9.
International Search Report with Written Opinion corresponding to International Patent Application No. PCT/EP2010/066271, mailed Jan. 25, 2011.
Clemens et al. (1983) "A simple method for generation of antibodies with specificity for 1, 25-Dihydroxyergocalciferol and 1, 25-Dihydroxycholecalciferol," Steroids. 42(5):503-509.
Hollis et al. (1993) "Determination of vitamin D status by radioimmunoassay with an 125I-labeled tracer," Clin. Chem. 39;529-533.
Immundiagnostik AG "25(OH) Vitamin D3 Antibody, monoclonal," ImmunDiagnostik Data Sheet. Accessible on the Internet at URL: http://www.immundiagnostik.com/fileadmin/pdf/A%201025.pdf. [Last Accessed Jul. 7, 2014].
Immundiagnostik AG (2005) "Newsletter, 2005: Products" ImmunDiagnostik AG Product Listing for 2005.
Kobayashi et al. (1994) "Production of a group-specific antibody to 1, 125-dihydroxyvitamin D and its derivatives having 1,3-dihydroxyated A-ring structure," Steroids. 59:401-411.
Kobayashi et al. (1997) "Production and Characterization of Monoclonal Antibodies against Two Haptenic Derivatives of 1, 25-Dihydroxyvitamin D3 Conjugted with Bovine Serum Albumin throughthe C-3 or C-2 Position,".
Perry et al. (1983) "Monoclonal antibody with high affinity for 1,25-dihydroxycholecalciferol," Biochem. Biophys.
Zerwekh (2008) "Blood biomarkers of vitamin D status," Am. J. Clin. Nutr. 87(4):1087S-1091S.

PROCESS FOR THE PRODUCTION OF A HYBRIDOMA AND ANTIBODY OBTAINED THEREFROM, ABLE TO RECOGNIZE MORE THAN ONE VITAMIN D METABOLITE

CROSS REFERENCE TO RELATED APPLICATION

This application is a Continuation of U.S. patent application Ser. No. 12/911,294 filed Oct. 26, 2010 which claims the benefit of U.S. Provisional Patent Application No. 61/255,164, filed Oct. 27, 2009, of PCT Patent Application No. PCT/EP2009/064148, filed Oct. 27, 2009, and Belgian Provisional Patent Application No. BE 2010/0234, filed Apr. 12, 2010, each of which is incorporated herein by reference into its entirety.

BACKGROUND OF THE INVENTION

Field of the Invention

The invention concerns a process for the production of a hybridoma and a monoclonal antibody obtained therefrom, able to recognize one epitope present on more than one antigen. In particular, the invention relates to a process for the production of a hybridoma and a monoclonal antibody, or fragments thereof, able to recognize more than one vitamin D metabolites, namely 25-hydroxyvitamin $D_2$ and 25-hydroxyvitamin $D_3$.

Description of Related Art

Vitamin D is the generic term used to designate vitamin $D_2$ or ergocalciferol and vitamin $D_3$ or cholecalciferol. Humans naturally produce vitamin $D_3$ when the skin is exposed to ultraviolet sun rays. Vitamin $D_3$ is transferred to the liver, where it is metabolised into 25-hydroxyvitamin $D_3$, which is the main form of vitamin D circulating in the body. Since the nineteenth century, vitamin $D_2$ has been available orally through food in order to compensate for a lack of vitamin $D_3$ for example among people who are hardly exposed to sunlight. The oral consumption of vitamin $D_2$ has become increasingly important over recent centuries. In fact, it is currently known that vitamin D has a primary role in the body for calcium binding, and mineralization of bones. It also plays a significant role in various metabolic pathways. The 25-hydroxyvitamin D, and particularly 25-hydroxyvitamin $D_2$ and 25-hydroxyvitamin $D_3$ are the forms of vitamin D which are most easily accumulated in the body. These two precursors can be converted by the kidneys to form $1\alpha,25$-dihydroxyvitamin D, which is the biologically active form. 1,25-dihydroxyvitamin D relates to the active forms of vitamin D (also known as D hormones) which have a hydroxyl grouping in positions 1 and 25 of the formula (A) and (B). More than fifty or so different metabolites of vitamin D have been discovered to date. Among these are 24,25-dihydroxyvitamin D and 25,26-dihydroxyvitamin D.

It is important to ensure the content of vitamin D in the body can be measured. However, measuring the content of vitamin D is actually of little value, since vitamin D concentrations fluctuate significantly based on the oral consumption of vitamin $D_2$. The same applies equally as regards the physiologically active forms of vitamin D ($1\alpha,25$-dihydroxyvitamin D), which are also present in the body in relatively low quantities and fluctuate significantly in comparison to 25-hydroxyvitamin D. For these reasons, the quantification of 25-hydroxyvitamin D (25-hydroxyvitamin $D_2$ and 25-hydroxyvitamin $D_3$) is a valuable tool to facilitate the overall analysis of vitamin D in an individual. Various methods exist, some of which involve immunology, to determine the presence of 25-hydroxyvitamin D.

Usually, immunological methods involve the use of polyclonal antibodies, or monoclonal antibodies. Polyclonal antibodies are known from a long time. To obtain such polyclonal antibodies, animals (such as rabbits for instance) need to be immunised with a highly purified preparation of an antigen. The immunisation has to be done repeatedly with such purified preparation. However, most frequently, this leads to the production of a mixture of antibodies, this mixture randomly binding more than one antigen, thus leading to unspecific measurement. A first issue is the life span of the host animal, Frequently, multiple animals needed to be immunised because of biological variability, Some animals being the source of the most specific antisera have to be selected and the death of said animals lead to the end of the production of the desired antibodies, until next immunisation of animals. Secondly, the antiserum reactivity is also a concern because the desired antibody is only a fraction of the total antibodies in the serum, which is itself a too heterogenic mixture. Further, the technique suffers from batch-to-batch variability. However, the production of polyclonal antibodies is a quick and inexpensive technique which has been and is still widely used in immunology.

In the field of recognition of vitamin D metabolites, a lot of documents describing the use of polyclonal antibodies are known. For instance, Hollis et al. (Clinical chemistry, 1993, 39, 529-533), EP 0092004, Kobayashi et al. (Steroids, 1994, 59, 401-411), and Clemens et al. (Steroids, 1983, 42, 503-509) disclose the production of polyclonal antibodies and their use in vitamin D radioimmunoassay.

In WO 2007/039193, Roche Diagnostics GmbH and F. HOFFMANN-LA ROCHE AG describe various methods of the state of the art. The latter disclose a process to produce polyclonal antibodies against 25-hydroxyvitamin D, which includes steps of immunising an animal with a conjugate which contains 25-hydroxyvitamin $D_3$ or 25-hydroxyvitamin $D_2$ as a hapten, isolating the serum or plasma of this animal and purifying the antibodies contained in the serum or the plasma by immunosorption on a complementary matrix, which includes 25-hydroxyvitamin $D_2$ when the hapten is 25-hydroxyvitamin $D_3$ or which includes 25-hydroxyvitamin $D_3$ when the hapten is 25-hydroxyvitamin $D_2$. EAH-Sepharose has been used as the preferred material for the immunosorption matrix. One major problem arising with this method is that the antibodies are polyclonal, namely that new immunisations must be performed on an animal to produce them. Another problem is that if the method does indeed allow both 25-hydroxyvitamin $D_2$ and 25-hydroxyvitamin $D_3$ to be determined in a sample, it is necessary to carry out two test batteries involving polyclonal antibodies to find the total amount of the two components of 25-hydroxyvitamin D, i.e. one test to determine the amount of 25-hydroxyvitamin $D_2$ in the sample and another one to determine the amount of 25-hydroxyvitamin $D_3$ in the same sample.

For the quantification of a molecule in biological samples, for instance in diagnostic kits, monoclonal antibodies can also be used. The Kohler and Milstein's invention dated 1975 opened a totally new field in immunology through a technique involving the fusion, in the presence of polyethylene glycol, of a myeloma cell rendered drug sensitive through a mutation in gene HGPRT with immune spleen B cells from a host animal immunised with the antigen of interest. Hybridoma cells survive and may be cultured in an appropriate medium (HAT) and rendered immortal. Because each hybridoma descends from one B cell, it makes copies of only one monoclonal antibody. The hybridoma that produces the antibody of interest is grown in culture to produce large amounts of monoclonal antibody, which are then isolated for further use. It is worth noting that monoclonal antibody is known to be highly specific antibodies against one epitope.

In the field of recognition of metabolites of vitamin D, monoclonal antibodies are used too. For instance Perry et al. (Biochemical and biophysical research communications, 1983, 112, 431-436), U.S. Pat. No. 4,585,741 and Kobayashi et al. (Biol. Pharm. Bull., 1997, 20(9), 948-953) disclose the use monoclonal antibodies against 1,25 dihydroxycholecalciferol. It is worth noting that the normal production scheme of a monoclonal antibody directed against one specific antigen includes the use of one hapten, the immunisation of one animal (generally a mouse), that after fusion between spleen cell and myeloma cell, one hybridoma is produced, and this latter may be cultured and immortalized to produce one monoclonal antibody specifically directed against a single epitope on a single antigen.

If one skilled in the art would like to use monoclonal antibodies for the detection of more than one antigen, he must produce in two parallel processes a monoclonal antibody for each molecule to be detected. For example WO 03/104820 discloses the quantification of vitamins A and $D_3$ in fluid samples. A monoclonal antibody against vitamin A is produced using standard procedures from vitamin A-KLH conjugate (i.e. the hapten is vitamin A). A monoclonal antibody against vitamin $D_3$ is produced from vitamin $D_3$-KLH conjugate (i.e. the hapten is vitamin $D_3$). Hence, two tests have to be performed to obtain the amount of both vitamins in the fluid samples.

SUMMARY OF THE INVENTION

It has now been found that the process according to the invention allows a monoclonal antibody produced by one and the same hybridoma to be able to recognize one epitope present on more than one antigen, which is contrary to all expectations in the art. In particular, the inventors have found that both 25-hydroxyvitamin $D_2$ and 25-hydroxyvitamin $D_3$ bind a monoclonal antibody issued from a single hybridoma.

For the sake of clarity, although it should be understood that, within the frame of the present invention, a given hybridoma produces a given type of monoclonal antibody, i.e. in practice several molecules of the same structure, in the present text, when speaking about the invention, one will use "monoclonal antibody" to designate the production of monoclonal antibody from a single hybridoma, and "monoclonal antibodies" to designate the production of monoclonal antibody from different hybridomas.

Unless otherwise specified, the term "vitamin D" must be understood within the context of the present document as including the forms of vitamin $D_2$ and vitamin $D_3$ with the following formula (A) and (B):

Formula (A)

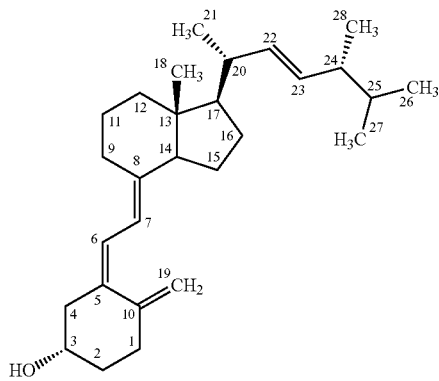

Formula (B)

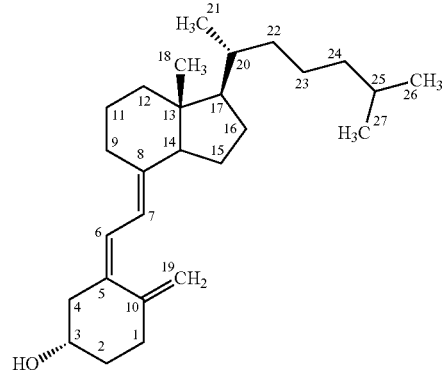

In formula (A) and (B), the positions of vitamin D are reflected in the nomenclature of the steroids. 25-hydroxyvitamin D indicates the vitamin D metabolites which are hydroxylated at position 25 of the formula (A) and (B), namely 25-hydroxyvitamin $D_2$ as well as 25-hydroxyvitamin $D_3$. As above-mentioned, 25-hydroxyvitamin $D_2$ and 25-hydroxyvitamin $D_3$ are particularly relevant forms of vitamin D when used for diagnostic purposes.

The vitamin D metabolites are not immunogen as such. The chemical activation of the components resulting from the metabolism of vitamin D as well as their binding to carrier proteins or linked groups is significant. Therefore, to ensure successful immunisation, it is vital to prepare a conjugate which may contain a metabolite of vitamin D or a derivative thereof as a hapten. The term "a hapten" must be understood by a person skilled in the art as a substance which is not immunogenic in itself, but which, by coupling with a carrier protein, is revealed in a form against which antibodies can be generated. Carrier proteins for the production of conjugates of haptens, i.e. immunogens, are known to those of ordinary skill in the art. The bovine serum albumin (BSA), the β-galactosidase or the keyhole limpet hemocyanine (KLH) are currently used as carrier proteins. The term "carrier protein" refers to a protein which transports a specific substance or a group of substances though the cellular membrane, in extra-cellular fluids or in an intracellular compartment.

Only position 3 of the structures such as represented in formula (A) and (B) is, in principle, suitable for the activation and coupling of the carrier proteins. In fact, the vitamin D metabolites are believed to bind via position 3 (see WO 2007/039194; Kobayashi and al. "Production and specificity of antisera raised against 25-hydroxyvitamin $D_3$-[C-3]-bovine serum albumin conjugates", Steroids 1992, 57(10), pp. 488-493).

According to a first aspect, the present invention relates to a process for the production of a hybridoma, and of a monoclonal antibody, or fragments thereof, able to recognize 25-hydroxyvitamin $D_2$ and 25-hydroxyvitamin $D_3$, comprising the following steps:

a) Immunisation of an animal with a hapten, rendered immunogenic, of general formula (I), or a salt thereof, or a derivative thereof in which the carboxylic acid function is protected to form an ester, amide or oxazoline,

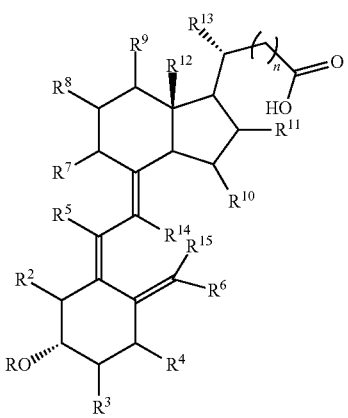

(I)

wherein n is an integer between 0 and 3;

$R^2$, $R^3$, $R^4$, $R^5$, $R^6$, $R^7$, $R^8$, $R^9$, $R^{10}$, $R^{11}$, $R^{14}$, $R^{15}$ are independently hydrogen or a $C_{1-4}$ alkyl;

$R^{12}$ and $R^{13}$ are a $C_{1-4}$ alkyl;

R is a hydrogen or a substituent selected from the group consisting of a group of acyl, benzyl, alkyl, aryl, alkyl ether, dimethoxytrityl, methoxytrityl, tetrahydropyranyl, triphenylmethyl groups, and a silyl derivative;

b) sampling of B cells produced by the animal and fusion thereof with myeloma cells to form the hybridoma;

c) production, from at least part of the obtained hybridoma, of a monoclonal antibody, or fragments thereof, able to recognize 25-hydroxyvitamin $D_2$ and 25-hydroxyvitamin $D_3$.

The present process allows to produce a monoclonal antibody able to bind or recognize 25-hydroxyvitamin $D_2$ and 25-hydroxyvitamin $D_3$ (two different molecules) from a hybridoma obtained by immunisation with a single hapten renders immunogenic, i.e. with a single conjugate. This is a totally unexpected result which could not be suggested by prior art. Indeed, as previously mentioned, it is known in the art that a monoclonal antibody specifically binds one antigen which is similar to the hapten used. Herein, the present invention surprisingly discloses a monoclonal antibody binding two different antigens, said monoclonal antibody being produced by a hybridoma provided by immunisation with a single hapten of general formula (I).

The hapten of general formula (I) may be in the form of a carboxylate salt. Organic or Inorganic salts may be convenient. Therefore, the salts used can be, for example, sodium, potassium or ammonium salts. Alternatively, the hapten of general formula (I) may be a derivative in which the carboxylic acid function may be protected to form an ester, amide or oxazoline. The ester may be an alkyl-, aryl-, benzylic-, thio-, seleno-, silyl- or ortho-ester.

In the present invention, the term "$C_{1-4}$alkyl" refers to a hydrocarbon radical having the formula $C_mH_{2m+1}$ in which m is an integer between 1 and 4. For example the term "$C_{1-4}$alkyl" refers to methyl, ethyl, n-propyl, i-propryl, n-butyl, i-butyl, s-butyl and t-butyl radical. The term "acyl" refers to a radical of formula $T^1C(O)$— in which $T^1$ is a substituent alkyl or aryl. The term "benzyl" refers to a radical of formula $T^2CH_2$—in which $T^2$ is an aryl group. The term "alkyl ether" refers to a radical of formula $T^3OT^4$— in which $T^3$ is an alkyl, an aryl or a benzyl and $T^4$ a hydrocarbon chain of formula —$(CH_2)_p$— in which p is an integer between 1 and 10. The term "dimethoxytrityl" refers to the radical bis-(4-methoxyphenyl)phenylmethyl. The term "methoxytrityl" refers to the radical 4-methoxyphenyl)diphenylmethyl.

The term "aryl" according to the present invention refers to an aromatic hydrocarbon, polyunsaturated group, with one or more fused rings (for example napthyl) or covalently bound, generally containing between 6 and 10 carbon atoms, in which at least one cycle is aromatic. The rings can be substituted. Non-exhaustive examples include phenyl, napthyl, anthracyl and biphenyl groups.

The term "substituted" as used in the present invention indicates that one or more hydrogens of the atom indicated in the expression using "substituted" is replaced with a selection from the Indicated group, subject to the valency of the atom(s) indicated not exceeding the normal valency of the same, and that the substitution results in a chemically stable compound, namely a compound sufficiently robust to survive in a clearly identifiable form and to an acceptable degree of purity from the reaction mixture. Substituents can be selected, but not limited to, from the group consisting of alkyl, aryl, cycloalkyl, halide, hydroxyl, nitro, amido, carboxy, amino and cyano groups. In the present invention, the term "nitro" refers to the group —$NO_2$. In the present invention, the term "cyano" refers to the group —CN. In the present invention, the term "hydroxyl" refers to the group —OH. In the present invention, the term "amido" refers to the group —C(O)—NH—. In the present invention, the term "carboxy" refers to the group —C(O)O—. In the present invention, the term "halide" refers to the chloride, fluoride, bromide and iodide radicals. In the present invention, the term "amino" refers to the radical of a trivalent nitrogen atom substituted or not. In the present invention, the term "cycloalkyl" refers to a cyclic alkyl group including all the hydrocarbon groups containing one or two rings, including monocyclic or bicyclic groups. The cycloalkyls include at least three carbon atoms in the cycle, preferably between 3 and 10 carbon atoms and can be optionally substituted.

The term "alkyl" refers to a radical hydrocarbon of formula $C_mH_{2m+1}$ in which m is an integer greater than 1. Generally, the alkyl groups of the present invention include between 1 and 10 carbon atoms. For example, the term "$C_{1-10}$ alkyl" refers but is not limited to a radical methyl, ethyl, n-propyl, i-propyl, n-butyl, i-butyl, s-butyl, t-butyl, 1-pentyl, 2-pentyl, 3-pentyl, i-pentyl, neo-pentyl, t-pentyl, 1-hexyl, 2-hexyl, 3-hexyl, 1-methyl-1-ethyl-n-pentyl, 1,1,2-tri-methyl-n-propyl, 1,2,2-trimethyl-npropyl, 3,3-dimethyl-n-butyl, 1-heptyle, 2-heptyle, 1-ethyl-1,2-dimethyl-n-propyl, 1-ethyl-2,2-dimethyl-n-propyl, 1-octyle, 3-octyle, 4-methyl-3-n-heptyle, 6-methyl-2-n-heptyle, 2-propyl-1-n-heptyle, 2,4,4-trimethyl-1-n-pentyl, 1-nonyle, 2-nonyle, 2,6-dimethyl-4-n-heptyle, 3-ethyl-2,2-dimethyl-3-n-pentyl, 3,5, 5-trimethyl-1-n-hexyl, 1-decyle, 2-decyle, 4-decyle, 3,7-dimethyl-1-n-octyle, 3,7-dimethyl-3-n-octyle. The alkyl group may be substituted.

The term "tetrahydropyranyl" refers to a radical of 2-tetrahydropyrane.

The term "triphenylmethyl" refers to a radical methyl substituted by three aryl groups, preferably phenyl.

The term "silyl derivative" refers to a radical of formula $T^5T^6T^7Si$— in which $T^5$, $T^6$, $T^7$ are independently an alkyl, aryl, alkoxy and aryloxy. In the present invention, the term "alkoxy" refers to a radical of formula —$OT^8$ in which $T^8$ is an alkyl substituted or not. In the present invention, the term "aryloxy" refers to a radical of formula —$OT^9$ in which $T^9$ is an aryl substituted or not.

Said hapten may be rendered immunogen by a covalent coupling with an immunogenic carrier protein, by encapsulation in the liposomes, by anchorage in the liposomes, by coupling of said hapten with a polymer, by induction with a biopolymer, or by coupling with a multiple antigenic peptide. The term "immunogen" refers to a substance likely to trigger an immune reaction. Unlike the immunogen, the hapten is a derivative which can be identified by the immune system (for example antibodies) but which does not trigger any immune reaction.

When said hapten is covalently bound with an immunogenic carrier protein, said carrier protein may be BSA (bovine serum albumin), ovalbumin, HSA (human albumin serum), THY (thyroglobulin), KLH (keyhole limpet hemocyanine), cBSA (bovine cationic albumin), β-galactosidase or CCH (Concholepas hemocyanine).

When said hapten is bonded to a polymer, said polymer may be a synthetic, natural or modified natural polymer. Therefore, the synthetic polymer may be, but not limited to, for example poly-L-lysine or agarose. Alternatively, the natural polymer maybe, but not limited to, dextrane. Alternatively, the modified natural polymer may be, but not limited to, carboxymethyl cellulose.

Alternatively, said hapten may be rendered immunogenic by induction with a biopolymer. The process is described in the publication Basalp and al. "Immunogenic $Cu^{2+}$—induced Biopolymer systems comprising a steroid hormone, protein antigen, and synthetic polyelectrolytes (Hybridoma and Hybridomics, 2002, 21(1), pp. 45-51).

Alternatively, said hapten may be bonded to a multiple antigenic peptide. Said multiple antigenic peptides may be a polylysine core to which 2 to 16 copies of a synthetic peptide are bonded.

Preferably, said hapten is rendered immunogenic by a covalent coupling with a carrier protein. The KLH and BSA may be particularly effective carrier proteins for the process and use of the present invention. The coupling between the hapten and the carrier protein may be performed via the carboxylic acid function of the hapten.

Preferably, the hapten may be a derivative of general formula (I) in which n is equal to 0. In particular, said hapten may be the derivative of general formula (I), in which n is equal to 0 and in which R, $R^2$, $R^3$, $R^4$, $R^5$, $R^6$, $R^7$, $R^8$, $R^9$, $R^{10}$, $R^{11}$, $R^{14}$, $R^{15}$ are respectively hydrogen; $R^{12}$ and $R^{13}$ are respectively methyl group. Therefore, the name of such hapten according to the IUPAC standard is the (2S)-2-((7aR,E)-4-((Z)-2-((S)-5-hydroxy-2-methylenecyclohexylidene)ethylidene)-7a-methyloctahydro-1H-inden-1-yl)propanoic acid. This compound can also be named acid 23,24,25,26,27-pentanor-9,10-secocholesta-5,7,10(19)-trien-3β-ol-22-oic, the CAS number of which is 99518-38-4.

Alternatively, the hapten may be a derivative of general formula (I) in which n is equal to 1. In particular, said hapten may be the derivative of general formula (I) in which n is equal to 1 and in which R, $R^2$, $R^3$, $R^4$, $R^5$, $R^6$, $R^7$, $R^8$, $R^9$, $R^{10}$, $R^{11}$, $R^{14}$, $R^{15}$ are respectively hydrogen; $R^{12}$ and $R^{13}$ are respectively methyl group. Therefore, the name of such hapten according to the IUPAC standard is the acid (R)-3-((1R,3aS,7aR,E)-4-((Z)-2-((S)-5-hydroxy-2-methylenecyclohexylidene)-ethylidene)-7a-methyloctahydro-1H-inden-1-yl)butanoic. This compound can also be named acid 24,25,26,27-tetranor-9,10-secocholesta-5,7,10(19)-trien-3β-ol-23-oic, the CAS number of which is 76794-34-8.

Alternatively, the hapten may be a derivative of general formula (I) in which n is equal to 2. In particular, said hapten may be the derivative of general formula (I) in which n is equal to 2 and in which R, $R^2$, $R^3$, $R^4$, $R^5$, $R^6$, $R^7$, $R^8$, $R^9$, $R^{10}$, $R^{11}$, $R^{14}$, $R^{15}$ are respectively hydrogen; $R^{12}$ and $R^{13}$ are respectively methyl group. Therefore, the name of such hapten according to the IUPAC standard is the acid (R)-4-((1R,3aS,7aR,E)-4-((Z)-2-((S)-5-hydroxy-2-methylenecyclohexylidene)ethylidene)-7a-methyloctahydro-1H-inden-1-yl)-pentanoic. This compound can also be named acid 25,26,27-trinor-9,10-secocholesta-5,7,10(19)-trien-3β-ol-24-oic.

Alternatively, the hapten may be a derivative of general formula (I) in which n is equal to 3. In particular, said hapten may be the derivative of general formula (I) in which n is equal to 3 and in which R, $R^2$, $R^3$, $R^4$, $R^5$, $R^6$, $R^7$, $R^8$, $R^9$, $R^{10}$, $R^{11}$, $R^{14}$, $R^{15}$ are respectively hydrogen; $R^{12}$ and $R^{13}$ are respectively methyl group. Therefore, the name of such hapten according to the IUPAC standard is the acid (R)-5-((1R,3aS,7aR,E)-4-((Z)-2-((S)-5-hydroxy-2-methylenecyclohexylidene)ethylidene)-7a-methyloctahydro-1H-inden-1-yl)-hexanoic. This compound can also be named acid 26,27-bisnor-9,10-secocholesta-5,7,10(19)-trien-3β-ol-25-oic.

Preferably, the hybridoma produced following the fusion of the myeloma with the B cells of the animal can be chosen in the group consisting of the hybridomas deposited in the BCCM/LMBP (BCCM/LMBP® Belgian Coordinated Collections of Microorganisms—Department of Biomedical Molecular Biology—Ghent, Belgium) on Sep. 21, 2009 under deposit numbers LMBP 7011CB, LMBP 7012CB and LMBP 7013CB, and hybridomas deposited in the BCCM/LMBP on Mar. 9, 2010 under deposit numbers LMBP 7205CB and LMBP 7204CB. The animal used for the experiments may be a rabbit, mouse, hamster, rat, and others.

Each of the monoclonal antibody produced by a single hybridoma of the present process is able to recognize 25-hydroxyvitamin $D_2$ and 25-hydroxyvitamin $D_3$. The recognition of 25-hydroxyvitamin $D_2$ and 25-hydroxyvitamin $D_3$ may be simultaneous. The term "simultaneous" means that a monoclonal antibody produced by the process of the present invention is able to bind or recognize both 25-hydroxyvitamin $D_2$ and 25-hydroxyvitamin $D_3$ when both antigens are present in the same sample. Therefore, the recognition percentage of the 25-hydroxyvitamin $D_2$ and 25-hydroxyvitamin $D_3$ may be between 70 and 110%. The recognition percentage is the ratio, multiplied by 100, between the total quantity of 25-hydroxyvitamin $D_2$ and 25-hydroxyvitamin $D_3$ recognized by the antibody according to the invention and the total effective quantity of 25-hydroxyvitamin $D_2$ and 25-hydroxyvitamin $D_3$ present in the sample to be tested. The percentage may exceed 100%. This is due to the uncertainty associated with the method of measuring overall quantities of 25-hydroxyvitamin $D_2$ and 25-hydroxyvitamin $D_3$. This is a phenomenon well known to those of ordinary skill in the art for this type of measurement.

According to a second aspect of the invention, several hybridomas each able to produce a monoclonal antibody or fragments thereof able to recognize 25-hydroxyvitamin $D_2$ and 25-hydroxyvitamin $D_3$ are provided. A hybridoma may be obtainable by the steps of a) and b) of the present process. The hybridoma can be chosen in the group consisting of the hybridomas deposited in the BCCM/LMBP (Belgian Coordinated Collections of Microorganisms—Department of Biomedical Molecular Biology—Ghent, Belgium) on Sep. 21, 2009 under deposit numbers LMBP 7011CB, LMBP 7012CB and LMBP 7013CB, and hybridomas deposited in the BCCM/LMBP on Mar. 9, 2010 under deposit numbers LMBP 7205CB and LMBP 7204CB. As stated above, each of these hybridomas is able to produce a monoclonal antibody, or fragments thereof, able to recognize 25-hydroxyvitamin $D_2$ and 25-hydroxyvitamin $D_3$. The recognition of the 25-hydroxyvitamin $D_2$ and 25-hydroxyvitamin $D_3$ by said monoclonal antibody, produced by a hybridoma according to the invention, may be simultaneous when the sample tested contains both 25-hydroxyvitamin $D_2$ and 25-hydroxyvitamin $D_3$. It is particularly remarkable that the monoclonal antibody, or the fragments thereof, produced by the hybridoma according to the invention may reveal a recognition percentage of 25-hydroxyvitamin $D_2$ and 25-hydroxyvitamin $D_3$ ranging from 70 to 110%. Said hybridoma may be used in the manufacturing of a diagnostic device able to recognize and quantify 25-hydroxyvitamin $D_2$ and 25-hydroxyvitamin $D_3$ in a sample or samples to be tested or may be used for the production of monoclonal antibody or fragments thereof able to recognize 25-hydroxyvitamin $D_2$ and 25-hydroxyvitamin $D_3$. Said hybridoma may be genetically engineered for enhancing the secretion of monoclonal antibody produced therefrom, i.e. plasmid or DNA sequence may be added to the DNA sequence of the hybridoma to form a genetically engineered hybridoma which can be used for producing monoclonal antibody able to recognize 25-hydroxyvitamin $D_2$ and 25-hydroxyvitamin $D_3$.

According to a third aspect of the invention, monoclonal antibody or fragments thereof is provided. Said monoclonal antibody or fragments thereof is able to recognize 25-hydroxyvitamin $D_2$ and 25-hydroxyvitamin $D_3$. Therefore, monoclonal antibody or fragments thereof against the two antigens 25-hydroxyvitamin $D_2$ and 25-hydroxyvitamin $D_3$ are provided. Preferably, said monoclonal antibody may be obtainable by the process of the present invention. Preferably, said monoclonal antibody or fragments thereof can be produced from a hybridoma selected from the group consisting of the hybridomas deposited in the BCCM/LMBP under deposit numbers LMBP 7011CB, LMBP 7012CB and LMBP 7013CB, and hybridomas deposited in the BCCM/LMBP on Mar. 9, 2010 under deposit numbers LMBP 7205CB and LMBP 7204CB. Each of these hybridomas is able to produce a monoclonal antibody, or fragments thereof, able to recognize 25-hydroxyvitamin $D_2$ and 25-hydroxyvitamin $D_3$.

The recognition, by said monoclonal antibody, of 25-hydroxyvitamin $D_2$ and 25-hydroxyvitamin $D_3$ may be simultaneous. Moreover, the recognition percentage of 25-hydroxyvitamin $D_2$ and 25-hydroxyvitamin $D_3$ may be between 70 and 110%.

According to a fourth aspect of the invention, the invention concerns the use of a hapten consisting of a compound of general formula (I), or a salt thereof, or a derivative thereof in which the carboxylic acid function is protected to form an ester, amide or oxazoline,

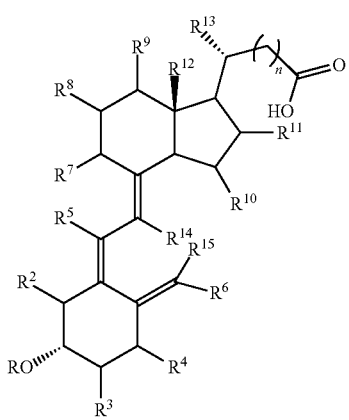

(I)

wherein
n is an integer between 0 and 3;
$R^2$, $R^3$, $R^4$, $R^5$, $R^6$, $R^7$, $R^8$, $R^9$, $R^{10}$, $R^{11}$, $R^{14}$, $R^{15}$ are independently hydrogen or a $C_{1-4}$ alkyl;
$R^{12}$ and $R^{13}$ are a $C_{1-4}$ alkyl;
R is a hydrogen or a substituent selected from the group consisting of an acyl, benzyl, alkyl, aryl, alkyl ether, dimethoxytrityl, methoxytrityl, tetrahydropyranyle, triphenylmethyl group, and a silyl derivative; said hapten rendered immunogenic;

for the production of a hybridoma, and of a monoclonal antibody or fragments thereof able to recognize 25-hydroxyvitamin $D_2$ and 25-hydroxyvitamin $D_3$. Alternatively, the hapten consisting of a compound of general formula (I) may be used for the production of recombinants monoclonal antibody fragments able to recognize 25-hydroxyvitamin $D_2$ and 25-hydroxyvitamin $D_3$. Said hapten may be used for the production of hybridoma according to steps a) and b) of the process of the present invention defined above. Said hapten may be used for the production of a monoclonal antibody according to the process of the present invention defined above.

Said hapten may be rendered Immunogenic by a covalent coupling with an immunogenic carrier protein, by encapsulation in the liposomes, by anchorage in the liposomes, by coupling of said hapten with a polymer, by induction with a biopolymer, or by coupling with a multiple antigenic peptide.

When said hapten is covalently coupled with an immunogenic carrier protein, said carrier protein may be the BSA (bovine serum albumin), ovalbumin, HSA (human serum albumin), THY (thyroglobulin), the KLH (Keyhole limpet hemocyanin), cBSA (cationic bovine serum albumin), β-galactosidase or CCH (Concholepas hemocyanine).

When said hapten is coupled to a polymer, said polymer may be a synthetic, natural or modified natural polymer. Therefore, the synthetic polymer may be, but not limited to, for example poly-L-lysine or agarose. Alternatively, the natural polymer maybe, but not limited to, dextrane. Alternatively, the modified natural polymer may be, but not limited to, carboxymethyl cellulose.

Alternatively, said hapten may be rendered immunogenic by induction with a biopolymer. The process is described in the publication Basalp and al. "immunogenic $Cu^{2+}$—induced Biopolymer systems comprising a steroid hormone, protein antigen, and synthetic polyelectrolytes" Hybridoma and Hybridomics, 2002, 21(1), 45-51, attached hereto in the reference.

Alternatively, said hapten may be coupled to a multiple antigenic peptide. Said multiple antigenic peptides may be a polylysine core where 2 to 16 copies of a synthetic peptide are coupled.

Preferably, said hapten is rendered immunogenic by a covalent bond with a carrier protein. The KLH and BSA can be particularly effective carrier proteins for the process and the use of the present invention. The coupling between the hapten and carrier protein may be performed via the carboxylic acid function of the hapten.

Preferably, the hapten used for the production of a hybridoma and monoclonal antibody obtained therefrom and able to recognize 25-hydroxyvitamin $D_2$ and 25-hydroxyvitamin $D_3$ may be a compound of formula (I) in which n is equal to 0. In particular, said hapten may be the acid (2S)-2-((7aR,E)-4-((Z)-2-((S)-5-hydroxy-2-methylenecyclohexylidene)ethylidene)-7a-methyloctahydro-1H-inden-1-yl)propanoic, namely the compound of formula (I) in which n is equal to 0; R, $R^2$, $R^3$, $R^4$, $R^5$, $R^6$, $R^7$, $R^8$, $R^9$, $R^{10}$, $R^{11}$, $R^{14}$, $R^{15}$ are respectively hydrogen; $R^{12}$ and $R^{13}$ are respectively methyl groups. Alternatively, the hapten used for the production of a hybridoma and monoclonal antibody obtained therefrom and able to recognize 25-hydroxyvitamin $D_2$ and 25-hydroxyvitamin $D_3$ may be the compound of formula (I) in which n is equal to 1. In particular, the hapten may be the acid (R)-3-((1R,3aS,7aR,E)-4-((Z)-2-((S)-5-hydroxy-2-methylenecyclo-hexylidene)ethylidene)-7a-methyloctahydro-1H-inden-1-yl)butanoic, namely the compound of formula (I) in which n is equal to 1; R, $R^2$, $R^3$, $R^4$, $R^5$, $R^6$, $R^7$, $R^8$, $R^9$, $R^{10}$, $R^{11}$, $R^{14}$, $R^{15}$ are respectively hydrogen; $R^{12}$ and $R^{13}$ are respectively methyl groups. Alternatively, the hapten used for the production of a hybridoma and monoclonal antibody obtained therefrom and able to recognize 25-hydroxyvitamin $D_2$ and 25-hydroxyvitamin $D_3$ may be the compound of formula (I) in which n is equal to 2. In particular, the hapten may be the acid (R)-4-((1R,3aS,7aR, E)-4-((Z)-2-((S)-5-hydroxy-2-methylenecyclohexylidene)-ethylidene)-7a-methyloctahydro-1H-inden-1-yl)pentanoic, namely the compound of formula (I) in which n is equal to 2; R, $R^2$, $R^3$, $R^4$, $R^5$, $R^6$, $R^7$, $R^8$, $R^9$, $R^{10}$, $R^{11}$, $R^{14}$, $R^{15}$ are respectively hydrogen; $R^{12}$ and $R^{13}$ are respectively methyl groups. Alternatively, the hapten used for the production of a hybridoma and monoclonal antibody obtained therefrom and able to recognize 25-hydroxyvitamin $D_2$ and 25-hydroxyvitamin $D_3$ may be the compound of formula (I) in which n is equal to 3. In particular, the hapten may be the acid (R)-5-((1R,3aS,7aR,E)-4-((Z)-2-((S)-5-hydroxy-2-methylenecyclohexylidene)-ethylidene)-7a-methyloctahydro-1H-inden-1-yl)hexanoic, namely the compound of formula (I) in which n is equal to 3; R, $R^2$, $R^3$, $R^4$, $R^5$, $R^6$, $R^7$, $R^8$, $R^9$, $R^{10}$, $R^{11}$, $R^{14}$, $R^{15}$ are respectively hydrogen; $R^{12}$ and $R^{13}$ are respectively methyl groups.

Therefore, the recognition of 25-hydroxyvitamin $D_2$ and 25-hydroxyvitamin $D_3$ by said monoclonal antibody, or the fragments thereof, may be simultaneous when both antigens are present in the same sample. Moreover, the recognition percentage of 25-hydroxyvitamin $D_2$ and 25-hydroxyvitamin $D_3$, by said monoclonal antibody or the fragments thereof, may be between 70 and 110%.

The hapten and/or monoclonal antibody, or the fragments thereof, according to the invention can be used in the manufacturing of a diagnostic device able to recognize and quantify 25-hydroxyvitamin $D_2$ and 25-hydroxyvitamin $D_3$ in a sample or samples to be tested. The hapten being a compound of general formula (I) such as defined above, may be used in the manufacturing of a diagnostic device able to recognize and quantify 25-hydroxyvitamin $D_2$ and 25-hydroxyvitamin $D_3$ in a sample to be tested. In this case, the recognition of 25-hydroxyvitamin $D_2$ and 25-hydroxyvitamin $D_3$ by said monoclonal antibody may be simultaneous when both antigens are in the same sample. The recognition percentage of 25-hydroxyvitamin $D_2$ and 25-hydroxyvitamin $D_3$ by said monoclonal antibody may be between 70 and 110%.

According to another aspect of the invention, a diagnostic device likely to allow the recognition and/or quantification of 25-hydroxyvitamin $D_2$ and 25-hydroxyvitamin $D_3$ in a sample to be tested is provided. The term "diagnostic device" as used herein also refers to a kit for the recognition and/or quantification of 25-hydroxyvitamin $D_2$ and 25-hydroxyvitamin $D_3$ in a sample. The sample may be a human or animal sample. Diagnostic device encompasses testing device for animal research. Said diagnostic device includes a monoclonal antibody or fragments thereof able to recognize 25-hydroxyvitamin $D_2$ and 25-hydroxyvitamin $D_3$. Preferably, the monoclonal antibody or the fragments thereof of said diagnostic device may be produced, according to the present invention, from a hybridoma selected from the group consisting of the hybridomas deposited in the BCCM/LMBP under deposit numbers LMBP 7011CB, LMBP 7012CB, LMBP 7013CB, LMBP 7204CB and LMBP 7205CB. The recognition of 25-hydroxyvitamin $D_2$ and 25-hydroxyvitamin $D_3$, by said monoclonal antibody or fragments thereof, may be simultaneous. Moreover, the recognition percentage of 25-hydroxyvitamin $D_2$ and 25-hydroxyvitamin $D_3$, by said monoclonal antibody or fragments thereof, may be between 70 and 110%. Said sample to be tested may be a biological sample from human or animal origin.

The diagnostic device may also include a sample of the compound of formula (I), or a salt thereof, or a derivative thereof in which the carboxylic acid function is protected to form an ester, amide or oxazoline,

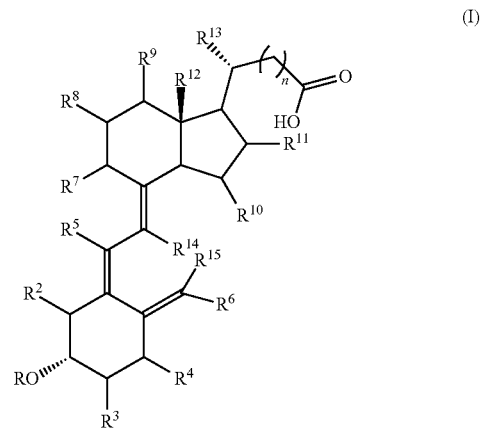

(I)

in which n is an integer between 0 and 3;

$R^2$, $R^3$, $R^4$, $R^5$, $R^6$, $R^7$, $R^8$, $R^9$, $R^{10}$, $R^{11}$, $R^{14}$, $R^{15}$ are independently hydrogen or a $C_{1-4}$ alkyl;

$R^{12}$ and $R^{13}$ are a $C_{1-4}$ alkyl;

R is a hydrogen or a substituent selected from the group consisting of an acyl, benzyl, alkyl, aryl, alkyl ether, dimethoxytrityl, methoxytrityl, tetrahydropyranyle, triphenylmethyl group, and a silyl derivative.

Preferably, the diagnostic device may include a sample of the compound of formula (I) in which n is an integer equal to 0; R, $R^2$, $R^3$, $R^4$, $R^5$, $R^6$, $R^7$, $R^8$, $R^9$, $R^{10}$, $R^{11}$, $R^{14}$, $R^{15}$ are respectively hydrogen; $R^{12}$ and $R^{13}$ are respectively methyl groups. Alternatively, the diagnostic device may include a sample of the compound of formula (I) in which n is an integer equal to 1; R, $R^2$, $R^3$, $R^4$, $R^5$, $R^6$, $R^7$, $R^8$, $R^9$, $R^{10}$, $R^{11}$, $R^{14}$, $R^{15}$ are respectively hydrogen; $R^{12}$ and $R^{13}$ are respectively methyl groups. Alternatively, the diagnostic device may include a sample of the compound of formula (I) in which n is an integer equal to 2; R, $R^2$, $R^3$, $R^4$, $R^5$, $R^6$, $R^7$, $R^8$, $R^9$, $R^{10}$, $R^{11}$, $R^{14}$, $R^{15}$ are respectively hydrogen; $R^{12}$ and $R^{13}$ are respectively methyl groups. Alternatively, the diagnostic device may include a sample of the compound of formula (I) in which n is an integer equal to 3; R, $R^2$, $R^3$, $R^4$, $R^5$, $R^6$, $R^7$, $R^8$, $R^9$, $R^{10}$, $R^{11}$, $R^{14}$, $R^{15}$ are respectively hydrogen; $R^{12}$ and $R^{13}$ are respectively methyl groups.

The diagnostic device may also include means of expression of a representative signal of the presence of 25-hydroxyvitamin $D_2$ and 25-hydroxyvitamin $D_3$ in a sample to be tested.

Said means of expression of a signal may be the tracer of formula (II),

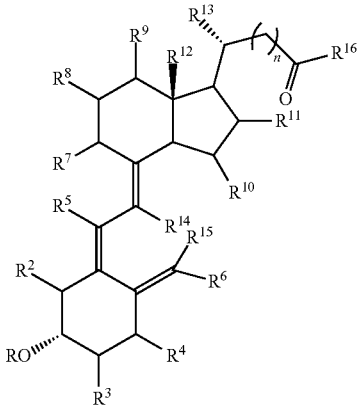

(II)

wherein
n is an integer between 0 and 3;
$R^2$, $R^3$, $R^4$, $R^5$, $R^6$, $R^7$, $R^8$, $R^9$, $R^{10}$, $R^{11}$, $R^{14}$, $R^{15}$ are independently hydrogen or a $C_{1-4}$ alkyl;
$R^{12}$ and $R^{13}$ are a $C_{1-4}$ alkyl;
R is a hydrogen or a substituent selected from the group consisting of an acyl, benzyl, alkyl, aryl, alkyl ether, dimethoxytrityl, methoxytrityl, tetrahydropyranyle, triphenylmethyl group, and a silylic derivative;
$R^{16}$ is the HRP protein (horseradish peroxidase), the alkaline phosphatase protein, the POD protein (peroxidase) or a group of formula (III) or (IV),

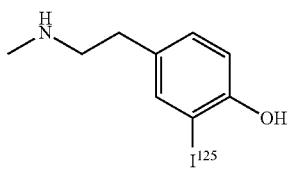

(III)

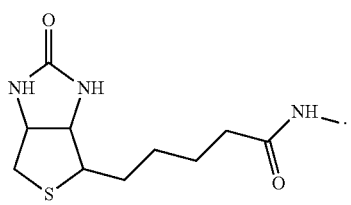

(IV)

The term "$I^{125}$" refers to a radio-isotope of the Iodine atom. The group (III) is bonded to the compound of formula (II) by its "amino" NH function. The group (IV) is bonded to the compound (II) by its "amido" C(O)NH— function. Alternatively, $R^{16}$ may be $^{125}$I-labeled histamine, $^{125}$I-labeled histidine, $^{125}$I-labeled tyrosine, $^{125}$I-labeled methyl tyrosinate, a fluorescent group, a chemiluminescent group or a group of formula (V)

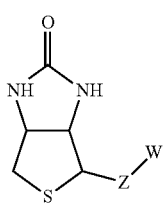

(V)

wherein Z is a linker and W is a functional group able to bind with a carbonyl group. Z may be a $C_1$-20 alkyl substituted or not. W may be amino, amido, hydroxyl, or hydrazine moiety.

Preferably, said tracer may be of formula (II),

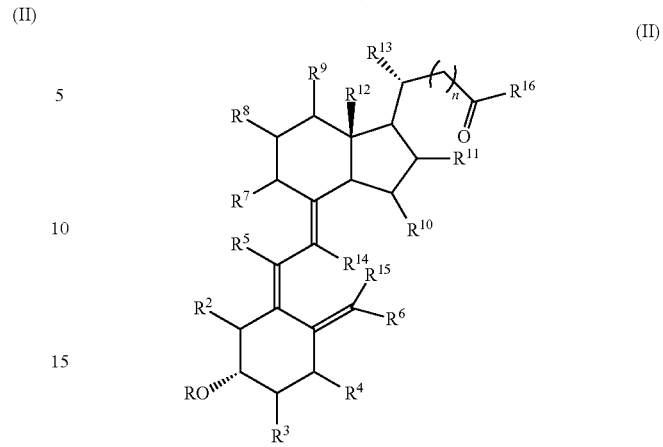

(II)

in which
n is an integer between 0 and 3; R, $R^2$, $R^3$, $R^4$, $R^5$, $R^6$, $R^7$, $R^8$, $R^9$, $R^{10}$, $R^{11}$, $R^{14}$, $R^{15}$ are hydrogen; $R^{12}$ and $R^{13}$ are a methyl group;
$R^{16}$ is a group of formula (III).
In particular, the diagnostic device may contain a sample of a tracer of formula (II) in which n is equal to 0; R, $R^2$, $R^3$, $R^4$, $R^5$, $R^6$, $R^7$, $R^8$, $R^9$, $R^{10}$, $R^{11}$, $R^{14}$, $R^{15}$ are hydrogen; $R^{12}$ and $R^{13}$ are a methyl group; $R^{16}$ is a group of formula (III).

Alternatively, said means of expression of a signal is a biosensor. This latter expressed a signal when a monoclonal antibody binds one antigen. The term "biosensor" refers to a physicochemical device able to detect a biological sample in a physicochemical, optical, piezoelectric, electrochemical, or electromagnetic manner. The biosensor notably includes a related electronic element, or signal processor allowing the handling or display of data, and a detecting element detecting physicochemical changes in the form of signals. The monoclonal antibody may be bonded to a support in the biosensor.

According to another aspect of the invention, the hapten of general formula (I) as defined above, rendered immunogenic, may be used for the production of a hybridoma. Said production of a hybridoma may comprise the steps of:
a) immunisation of an animal with a hapten, rendered immunogenic, of formula (I), or a salt thereof, or a derivative thereof in which the carboxylic acid function is protected to form an ester, amide or oxazoline,

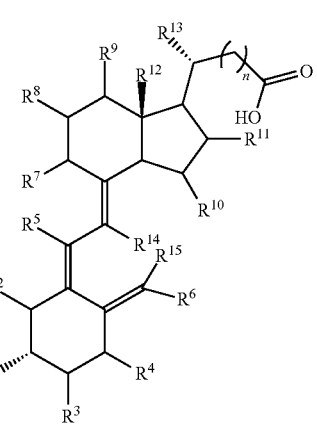

(I)

in which
n is an integer between 0 and 3;
$R^2$, $R^3$, $R^4$, $R^5$, $R^6$, $R^7$, $R^8$, $R^9$, $R^{10}$, $R^{11}$, $R^{14}$, $R^{15}$ are independently hydrogen or a $C_{1-4}$ alkyl,
$R^{12}$ and $R^{13}$ are a $C_{1-4}$ alkyl;

R is a hydrogen or a substituent selected from the group consisting of acyl, benzyl, alkyl, aryl, alkyl ether, dimethoxytrityl, methoxytrityl, tetrahydropyranyle, triphenylmethyl group, and a silyl derivative; and b) sampling of B cells produced by the animal and fusion of the same with myeloma cells to form the hybridoma. From a hybridoma obtained according to this process, a process for producing a monoclonal antibody, or fragments thereof, able to recognize, or directed against, 25-hydroxyvitamin $D_2$ and 25-hydroxyvitamin $D_3$ may be provided.

The fact that the monoclonal antibody obtained is able to identify 25-hydroxyvitamin $D_2$ and 25-hydroxyvitamin $D_3$ is extremely surprising and overcomes a technical obstacle whereby such property could not be obtained using a monoclonal antibody originating from a single hybridoma. A significant advantage of the process of the invention is that it allows the simultaneous recognition of 25-hydroxyvitamin $D_2$ and 25-hydroxyvitamin $D_3$ in a sample, in a simple procedure, which is also easily reproducible. In addition, this process responds to a long-unfulfilled industry need, despite the fact that technology in the field of monoclonal antibodies has been known for several decades.

DETAILED DESCRIPTION OF THE INVENTION

The present invention shall be described according to a specific form of execution in which the hapten, used for the immunisation of the animal, is a derivative of formula (I) in which n is an integer equal to 0; R, $R^2$, $R^3$, $R^4$, $R^5$, $R^6$, $R^7$, $R^8$, $R^9$, $R^{10}$, $R^{11}$, $R^{14}$, $R^{15}$ are hydrogen; $R^{12}$ and $R^{13}$ are a methyl group. This hapten shall be referred to as (H) for the remaining description. It is important to understand that the invention is not limited to this embodiment. For example, the hapten may be a derivative of formula (I) in which n is equal to 1, 2 or 3 with substituents unchanged.

Procedure for the Production of a Monoclonal Antibody

The production of a monoclonal antibody may be effected following the conventional procedure such as described, for example, in Kohler and Milstein, Nature 1975 (256), 495-497 or Eur. J. Immunol. 1976 (6), 511-519. According to this method, myeloid cells are combined with lymphocytic B cells of an immunised animal to obtain hybrid cells, known as a hybridoma, which produce a monoclonal antibody. In this procedure, a hapten is bonded to a carrier protein to form an immunogen which shall be capable of inducing immunogenicity. The carrier protein thus allows the hapten to gain the ability to trigger an immune reaction.

Synthesis of the Hapten and Preparation of the Immunogen

Therefore, in the present invention, the hapten (H), the synthesis of which is known to those of ordinary skill in the art, is initially coupled with the bovine serum albumin (BSA) according to the following protocol. In a medium including anhydrous dimethylformamide (Fluka 1386923-43408231), anhydrous dioxane (Aldrich S39136-277) and diisopropylethylamine (Fluka 03440), an amount of hapten (H) is activated for four hours at ambient temperature by the O—(N-Succinimidyl)-1,1,3,3-tetramethyluronium tetrafluoroborate (TSTU—Fluka 85972) dissolved in anhydrous dimethylformamide. Subsequently, 100 to 1000 hapten equivalents in solution are added to a BSA equivalent (Calbiochem 12659) diluted in carbonate buffer solution (0.1M; pH 9.4). The solution is stirred at ambient temperature for 18 h-away from exposure to light. The reactional mixture is then dialysed in a saline solution NaCl (9 g/l) for 48 h at 4° C. A fresh saline solution is re-introduced after 24 h.

The hapten (H) may also be coupled with KLH (Keyhole limpet hemocyanine, Sigma H2133). In this case, 20,000 to 500,000 equivalents of hapten in solution are added to a KLH equivalent diluted in the carbonate buffer solution (0.1M; pH 9.4). The solution is then stirred at ambient temperature for 18 h and away from exposure to light. The reaction mixture is then dialysed in a saline solution NaCl (9 g/l) for 48 h at 4° C. to obtain the desired immunogen. A fresh saline solution is re-introduced after 24 h.

Immunisation of the Animal

The female mice (6 weeks) used were provided by the CREAL company. The immunogen (20 µg in physiological saline solution) was injected subcutaneously in the mice with an additive (50% saline solution/50% additive (vol/vol)) which could be Freund's complete adjuvant (CFA, Difco Laboratories and reference: 263810) or Freund's incomplete adjuvant (IFA, Difco Laboratories and reference: 263910). The CFA is oil including killed mycobacteria. IFA is the same adjuvant as CFA without the mycobacteria. The adjuvant allows an immune response to be triggered in the body of the animal. After some injections of the immunogen (from 3 to 10), the serum of each immunised mouse was tested to monitor the serous content in terms of specific antibodies to the injected antigen. As soon as a mouse was considered positive (namely where the percentage binding of the radioactive-marked antigen or enzymatic marker achieved at least 10% when incubated with the mouse serum), it was selected for the cellular fusion carried out in the month following the serum test. During the fusion, the animal was euthanized (using $CO_2$), its spleen was extracted and the immunocompetent cells present in the spleen of the animal were retrieved by rubbing the spleen with flat-tipped forceps while perfusing it slowly with 10 ml of medium W/O kept at 37° C., namely a DMEM Dulbecco modified Eagle's Medium (GIBCO 21969) without protein and complemented with 2%(vol/vol) of a mixture 100× of penicillin and streptomycin. The cells thus sampled were transferred in a Petri dish, then in a sterile conical tube of 15 ml which was then centrifuged. The cell residue was then retrieved to be combined with the myeloid cells.

Myeloid Cells

Normally, the myeloma used for the fusion of mouse splenocytes are NSO myeloma (Sigma ref: 85110503), SP2/0-Ag14 (ATCC ref: CRL-1581) or P3X63Ag8.653 (ATCC ref: 1580). The myeloma were cultivated in a medium including a DMEM base mixture without additional protein of 2%(vol/vol) of a mixture 100× of penicillin and streptomycin, 2 to 5%(vol/vol) of glutamine, 2%(vol/vol) of non-essential amino acids (100×), 2%(vol/vol) of sodium pyruvate (100×), 1%(vol/vol) of gentamicine. The medium also included 10%(vol/vol) of foetal calf serum. The culture was centrifuged in the sterile conical tubes of 50 ml (at 1000 rpm, 10 minutes). The bases were gathered and centrifuged in a tube of 15 ml. Generally speaking, 1 ml of myeloma represents between $1\ 10^6$ and $2\ 10^8$ cells.

Cellular Fusion

The spleen cells were mixed with the myeloma cells, to form a hybridoma, with a ratio of around 5 to 10 spleen cells for 1 myeloma cell. In the present example: 4.7 ml of NSO myeloma at $3.4.10^6$ cells/ml were mixed with $8.10^7$ spleen cells. The mixture of spleen cells with myeloma cells was centrifuged and the supernatant removed. The cell residue thus obtained was slowly (1 minute) suspended in 1 ml of a polyethylene glycol solution 50%, with the temperature maintained at 37° C. for this operation. The polyethylene glycol solution was obtained by dissolving 5 g of polyethylene glycol (Merck, ref: 1.09727.0100) in 5 ml of phosphate buffer 0.1 M at pH 7.4, then adding 5%(vol/vol) of dimethylsulfoxide to the same (Sigma D2650) and sterilising by filtration (0.2 μm). The cell residue thus re-suspended in the PEG solution was diluted at least 10 times, by adding a W/O medium (DMEM without additional protein of 2%(vol/vol) of a mixture 100× of penicillin and streptomycin). The tube was centrifuged and the cell residue re-suspended in the HAT medium, including a DMEM base mixture without protein with added 2%(vol/vol) of a mixture 100× of penicillin and streptomycin, 2 to 5%(vol/vol) of glutamine, 2%(vol/vol) of non-essential amino acids (100×), 2%(vol/vol) of sodium pyruvate (100×), 1%(vol/vol) of gentamicine, 10%(vol/vol) of foetal calf serum, 2%(vol/vol) of hypoxanthine thymidine (50×), 2%(vol/vol) of aminopterine (50×), and finally 2%(vol/vol) of Nutridoma CS (Roche ref: 1363 743). The volume of HAT medium added to the cell residue was such that the spreading over the plates of 96 vessels was from $5\ 10^4$ to $10^5$ cells per vessel, based on 150 to 200 μl of medium per vessel. The plates were incubated for between 8 to 10 days, at 37° C. and with 5% $CO_2$.

Preselection of Hybridomas Each Producing a Hapten-Specific Antibody

The identification of wells from deep-well plates containing hybridoma producing monoclonal antibody able to recognize 25-hydroxyvitamin $D_2$ and 25-hydroxyvitamin $D_3$ was conducted using an RIA (Radio Immuno Assay) method during the homogenous phase, followed by an immunoprecipitation. This method consists of incubating a volume (between 50 and 100 μl) of the culture medium originating from the deep-well plates of the fusion, with a tracer of formula (II) in which n is equal to 0; R, $R^2$, $R^3$, $R^4$, $R^5$, $R^6$, $R^7$, $R^8$, $R^9$, $R^{10}$, $R^{11}$, $R^{14}$, $R^{15}$ are hydrogen; $R^{12}$ and $R^{13}$ are a methyl group; $R^{16}$ is a group of formula (III). After an incubation period of between 4 and 18 h, the reaction was stopped by the addition of SAC CEL (a cellulose suspension containing anti-mouse antibodies: IDS reference: AASAC4) to the medium. After centrifuging, the radioactivity of the bases was measured in a gamma counter. The positive wells (namely binding more than 10% of the total added radioactivity) are those which contained mouse antibodies specifically for the hapten (H), hence those containing specific hybridoma clones.

Selection of Hybridoma Clones Producing a Monoclonal Antibody Recognizing Both 25-Hydroxyvitamin $D_2$ and 25-Hydroxyvitamin $D_3$ Among the positive hybridomas (namely those producing monoclonal antibodies which identified the tracer) obtained, those identifying both 25-hydroxyvitamin $D_2$ and 25-hydroxyvitamin $D_3$ were selected by an inhibition test of the binding of said tracer. This test consisted of incubating the culture's supernatant (for example 100 μl) of the hybridoma (in a Petri dish) with the tracer (marked with iodine 125) and in the presence of 25-hydroxyvitamin $D_2$ or 25-hydroxyvitamin $D_3$. The mixture was incubated at ambient temperature for 18 h. The 25-hydroxyvitamin $D_2$ used was provided by Sigma under reference H17937, while the 25-hydroxyvitamin $D_3$ was provided by Sigma under reference H4014. The recognition tests were carried out with solutions of 25-hydroxyvitamin $D_2$ and 25-hydroxyvitamin $D_3$ at concentrations of 1000 ng/ml. The tracer was in solution in a mixture volume/volume: 25% water/25% ethanol/50% phosphate buffer 0.1M pH 7.4 CP (casein peptone: organotechnical reference: 1 9516) 10 g/l. The reaction was stopped by immunoprecipitation by adding SAC CEL (cellulose suspension containing anti-mouse antibodies: IDS reference: AASAC4) to the incubation medium.

Results

Table 1 represents the recognition results of 25-hydroxyvitamin $D_2$ and 25-hydroxyvitamin $D_3$ for selected hybridoma clones following preselection tests of hybridomas producing hapten-specific monoclonal antibodies.

TABLE 1

| Col 1 Clone No. | Without Vit. $D_2$ in Vit. $D_3$ Col 2 Fixation (%) | 25-OH-Vitamin $D_2$ 1 μg/ml | | 25-OH-Vitamin $D_3$ 1 μg/ml | |
|---|---|---|---|---|---|
| | | Col 3 Fixation (%) | Col 4 Inhibition (%) | Col 5 Fixation (%) | Col 6 Inhibition (%) |
| LMBP 7011CB | 63.2 | 47.2 | 25.3 | 9.4 | 85.2 |
| LMBP 7012CB | 60.0 | 10.0 | 83.3 | 0.9 | 98.5 |
| LMBP 7013CB | 48.6 | 30.6 | 36.9 | 18.3 | 62.3 |

TABLE 1-continued

|  | Without Vit. $D_2$ in Vit. $D_3$ | 25-OH-Vitamin $D_2$ 1 µg/ml | | 25-OH-Vitamin $D_3$ 1 µg/ml | |
|---|---|---|---|---|---|
| Col 1 Clone No. | Col 2 Fixation (%) | Col 3 Fixation (%) | Col 4 Inhibition (%) | Col 5 Fixation (%) | Col 6 Inhibition (%) |
| LMBP 7204CB | 57.1 | 23.6 | 58.6 | 28.5 | 50.1 |
| LMBP 7205CB | 68.7 | 42.0 | 38.0 | 51.8 | 24 |

The first column re presents the numbers of the tested clones, which correspond to the hybridoma deposited as described above. The second column corresponds to the percentage of binding of said tracer to the monoclonal antibody produced by the corresponding clone, in the absence of 25-hydroxyvitamin $D_2$ and 25-hydroxyvitamin $D_3$. The third column corresponds to the percentage of binding of said tracer to the monoclonal antibody produced by the corresponding clone in the presence of 25-hydroxyvitamin $D_2$ at a concentration in solution of 1 µg/ml. The fourth column corresponds to the inhibition percentage of corresponding monoclonal antibody in the presence of 25-hydroxyvitamin $D_2$ at a concentration of 1 µg/ml. This percentage is calculated by deducting from 100% the ratio, multiplied by 100, between the percentage of binding in the presence of 25-hydroxyvitamin $D_2$ at 1000 ng/ml and the percentage of binding without 25-hydroxyvitamin $D_2$. The fifth column corresponds to the percentage of binding of said tracer to the monoclonal antibody produced by the corresponding clone in the presence of 25-hydroxyvitamin $D_3$ at a concentration in solution of 1 µg/ml. The sixth column corresponds to the inhibition percentage of the corresponding monoclonal antibody in the presence of 25-hydroxyvitamin $D_3$ at a concentration of 1 µg/ml. This percentage is calculated by deducting from 100% the ratio, multiplied by 100, between the percentage of binding in the presence of 25-hydroxyvitamin $D_3$ at 1 µg/ml and the percentage of binding without 25-hydroxyvitamin $D_3$.

When the concentrations of 25-hydroxyvitamin $D_2$ and 25-hydroxyvitamin $D_3$ are around 1 µg/ml, the inhibition percentage of the monoclonal antibody produced by the clone LMBP7012CB may exceed 80% vis-à-vis 25-hydroxyvitamin $D_2$ and 25-hydroxyvitamin $D_3$.

Example of the Simultaneous Recognition of 25-Hydroxyvitamin $D_2$ and 25-Hydroxyvitamin $D_3$ A test of the simultaneous recognition of 25-hydroxyvitamin $D_2$ and 25-hydroxyvitamin $D_3$ was conducted on coated tubes. The monoclonal antibody was anchored in dry tubes (direct coating) at a concentration of 0.5 µg/ml. The antibody used was produced by the LMBP hybridoma 7013CB. Subsequently, 300 µl of incubation buffer (phosphate 50 mM pH7.4 casein peptone 2 g/l of sodium azide 0.5 g/l) and 100 µl of 25-hydroxyvitamin $D_2$ and 25-hydroxyvitamin $D_3$ were added to the tubes. The solutions were analysed after two hours at ambient temperature.

TABLE 2

| $D_3$ (ng/mL) | $D_2$ (ng/mL) | Total detected quantity (ng/mL) | Percentage of recognition (%) |
|---|---|---|---|
| 1.5 | 1.5 | 3.3 | 110 |
| 5 | 5 | 8.1 | 80 |
| 15 | 15 | 25.1 | 84 |
| 50 | 50 | 99.7 | 100 |

TABLE 2-continued

| $D_3$ (ng/mL) | $D_2$ (ng/mL) | Total detected quantity (ng/mL) | Percentage of recognition (%) |
|---|---|---|---|
| 50 | 5 | 60 | 110 |
| 5 | 50 | 42 | 75 |

The columns titled "$D_3$" and "$D_2$" in Table 2, respectively correspond to the concentrations, expressed in ng/mL, of 25-hydroxyvitamin $D_3$ and 25-hydroxyvitamin $D_2$ used for the recognition test. For example, when the concentrations of 25-hydroxyvitamin $D_2$ and 25-hydroxyvitamin $D_3$ were respectively 50 ng/ml, more than 99 ng/ml of 25-hydroxyvitamin $D_2$ and 25-hydroxyvitamin $D_3$ was detected, which represents a particularly noteworthy result.

Identical tests were carried out with the monoclonal antibody produced by the LBMP hybridoma 7012CB. Therefore, when the concentrations in 25-hydroxyvitamin $D_2$ and 25-hydroxyvitamin $D_3$ were each 1.5 ng/mL, the recognition percentage w as 86%. Similarly, when the concentrations of 25-hydroxyvitamin $D_2$ and 25-hydroxyvitamin $D_3$ were respectively 5 ng/mL, the recognition percentage was 77%. Excellent results were also obtained for other concentrations. Tests were also carried on with a monoclonal antibody produced from hybridomas LMBP 7204CB or LMBP 7205CB. When the concentrations in 25-hydroxyvitamin $D_2$ et 25-hydroxyvitamine $D_3$ were each 1,5 ng/mL, the recognition percentage was 104% with a monoclonal antibody from the hybridoma LMBP 7204CB. When the concentration in 25-hydroxyvitamin $D_2$ was 5 ng/mL and the concentration in 25-hydroxyvitamine $D_3$ was 50 ng/mL, recognition percentage was 100% with a monoclonal antibody from the hybridoma LMBP 7205CB. These two clones show an excellent recognition of 25-hydroxyvitamin $D_2$. The tests carried out with the monoclonal antibody produced by the hybridoma LMBP 7011CB also revealed good results.

Testing was also performed in human serum from patient. After a pre-treatment allowing the releasing of 25-hydroxyvitamin $D_2$ and 25-hydroxyvitamin $D_3$, the simultaneous recognition of 25-hydroxyvitamin $D_2$ and 25-hydroxyvitamin $D_3$ was conducted on coated tubes where the monoclonal antibody was anchored in dry tubes (indirect coating) at a concentration of 25 ng/ml. In table 3, the monoclonal antibody used was produced by the LMBP hybridoma 7013CB. In table 4, the monoclonal antibody used was produced by the LMBP hybridoma 7012CB. A reference method, LC-MS (Liquid Chromatography-Mass Spectrometry) has been used to validate the concentrations found in the human serum.

TABLE 3

| Human serum | [25OH Vit. $D_2$ + 25OHVit. $D_3$] ng/ml with Mab from 7013CB | [25OH Vit. $D_2$] ng/ml with LC-MS | [25OH Vit. $D_3$] ng/ml with LC-MS | [25OH Vit. $D_2$ + 25OH Vit. $D_3$] ng/ml with LC-MS | Recognition percentage |
|---|---|---|---|---|---|
| 1 | 50.3 | 10.7 | 48.0 | 58.7 | 86% |
| 2 | 91.4 | 124.2 | 0 | 124.2 | 74% |
| 3 | 52.3 | 14.3 | 47.8 | 62 | 84% |
| 4 | 120 | 28.0 | 95.6 | 123.6 | 97% |

TABLE 4

| Human serum | [25OH Vit $D_2$ + 25OH Vit $D_3$] ng/ml with Mab from 7012CB | [25OH Vit $D_2$] ng/ml with LC-MS | [25OH Vit $D_3$] ng/ml with LC-MS | [25OH Vit $D_2$ + 25OH Vit $D_3$] ng/ml with LC-MS | Recognition percentage |
|---|---|---|---|---|---|
| 5 | 42.8 | 4.1 | 38.4 | 42.5 | 101% |
| 6 | 20.9 | 6.8 | 13.6 | 20.4 | 102% |
| 7 | 43.1 | 10.5 | 36.8 | 47.3 | 91% |

Rat serum and mouse serum have been tested using the same protocol. Similar results were obtained.

Obtaining of Monoclonal Antibody

Following the selection of the clones of interest, the cells were frozen in liquid nitrogen for long-term preservation. The production of a monoclonal antibody is performed by a system of in vitro culture of hybridoma cells for example: in a spinner flask (Wheaton Magna-Flex® Microcarrier Spinner Flasks), or in CELLINE (Integra Bioscience) or any other method of in vitro culture suitable for hybridoma cells. Alternatively, the monoclonal antibody can be produced by an in vivo method, such as that featuring ascites, where permitted by law.

Purification of the Monoclonal Antibody

The culture's supernatant originating from the in vitro culture system of hybridoma cells is purified by affinity chromatography on a conventional column of protein A and/or protein G (GE Healthcare), on a STREAMLINE Protein A support (GE Healthcare).

Diagnostic Devices

The diagnostic devices according to the invention, also known as immunoassay devices can include "enzyme immunoassays" devices (EIA) or "enzyme-linked immunosorbent assays" devices (ELISA), an "immunofluorescence" device (IFA), a radiometric device or "radioimmunoassays" (RIA), a "magnetic separation assays" device (MSA), a "lateral flow assays" device, a "diffusion immunoassays" device, an immunoprecipitation device, an "immunosorbent" or "antigen-down assays" device, an immuno-agglutination device, a "chemilunescence immuno assay (CLIA)" device or also a device using a biosensor.

Various types of supports can be used: tubes, microtitration plates or blocks. The monoclonal antibody or the fragments thereof can be biotinylated to increase the binding or sensitivity to the different supports.

The monoclonal antibody, or fragments related to the same may be bound directly onto the support. It is also possible to bind an anti-mouse antibody to the support, followed by monoclonal antibody or fragments thereof according to the invention on this initial antibody. The monoclonal antibody or fragments thereof should preferably be biotinylated.

Alternatively, the hapten may be bound to the support. Subsequently, a monoclonal antibody according to the invention is added, followed by an anti-HRP secondary antibody. If required, the monoclonal antibody or fragments thereof can be used by direct binding to the HRP (horse radish peroxidase) in order to detect the immunogenic bound beforehand onto a support. Alternatively, the monoclonal antibody, or the fragments related to the same, can be biotinylated. Subsequently, the SAv-HRP (streptavidin—horse radish peroxidase) is added.

The tracer may be bound to a tyramine marked with iodine 125 for the RIA tests. It may also be used after biotinylation or binding to the HRP with a view to conducting ELISA or CLIA tests. The luminol or tetramethylbenzidine can subsequently be bonded to the HRP.

Finally, the tests can be performed in open or sealed automatic units.

In the competitive RIA tests, a fixed quantity of the tracer of formula (II) in which n is equal to 0; R, $R^2$, $R^3$, $R^4$, $R^5$, $R^6$, $R^7$, $R^8$, $R^9$, $R^{10}$, $R^{11}$, $R^{14}$, $R^{15}$ are hydrogen; $R^{12}$ and $R^{13}$ are a methyl group; $R^{16}$ is a group of formula (III), starts competing with the 25-hydroxyvitamin $D_2$ and 25-hydroxyvitamin $D_3$ present in the samples, controls or calibrators extracted for a fixed quantity of specific antibody, immobilised on the surface of a polystyrene support. After an incubation of 2 to 24 h at ambient temperature or at 37° C., an aspiration phase ends the competitive reaction. The tubes are then washed and the radioactivity is measured in a gamma counter.

Thanks to the present invention, the recognition of 25-hydroxyvitamin $D_3$ and 25-hydroxyvitamin $D_2$ is simultaneous when using diagnostic devices according to the Invention on samples containing 25-hydroxyvitamin $D_3$ and 25-hydroxyvitamin $D_2$.

The terms and descriptions used here are solely intended to be for reference and are not intended to be exhaustive. It is generally recognised that numerous variations are possible in the vein and breadth of the invention such as described in the claims which follow and their equivalents; in which all the terms must be understand as part of wider acceptance unless otherwise specified.

The invention claimed is:

1. A hybridoma suitable for the production of a monoclonal antibody able to recognize 25-hydroxyvitamin $D_2$ and 25-hydroxyvitamin $D_3$, wherein the hydridoma is selected from the group consisting of the hybridomas deposited in the BCCM/LMBP under deposit numbers LMBP 7011CB, LMBP 7012CB, LMBP 7013CB, LMBP 7204CB and LMBP 7205CB.

2. A monoclonal antibody, produced from a hybridoma selected from the group consisting of the hybridomas deposited in the BCCM/LMBP under deposit numbers LMBP 7011CB, LMBP 7012CB, LMBP 7013CB, LMBP 7204CB and LMBP 7205CB.

* * * * *